(12) United States Patent
Mikkaichi et al.

(10) Patent No.: US 8,540,706 B2
(45) Date of Patent: Sep. 24, 2013

(54) ORGAN INCISION METHOD

(75) Inventors: Takayasu Mikkaichi, Tokyo (JP); Takahiro Kogasaka, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 953 days.

(21) Appl. No.: 12/637,687

(22) Filed: Dec. 14, 2009

(65) Prior Publication Data
US 2010/0094284 A1 Apr. 15, 2010

Related U.S. Application Data

(62) Division of application No. 11/371,455, filed on Mar. 8, 2006, now abandoned.

(51) Int. Cl.
*A61B 18/12* (2006.01)

(52) U.S. Cl.
USPC .............................................. 606/39; 606/32

(58) Field of Classification Search
USPC ....................... 128/898; 606/32, 42, 45–47
See application file for complete search history.

(56) References Cited

U.S. PATENT DOCUMENTS

| | | | |
|---|---|---|---|
| 4,708,137 A | 11/1987 | Tsukagoshi | |
| 5,112,310 A * | 5/1992 | Grobe | 604/175 |
| 5,125,928 A | 6/1992 | Parins et al. | |
| 5,297,536 A | 3/1994 | Wilk | |
| 5,395,363 A | 3/1995 | Billings et al. | |
| 5,433,739 A | 7/1995 | Sluijter et al. | |
| 5,449,355 A * | 9/1995 | Rhum et al. | 606/41 |
| 5,458,131 A | 10/1995 | Wilk | |
| 5,486,161 A | 1/1996 | Lax et al. | |
| 5,637,090 A | 6/1997 | McGee et al. | |
| 6,059,719 A | 5/2000 | Yamamoto et al. | |
| 6,068,629 A | 5/2000 | Haissaguerre et al. | |
| 6,099,524 A | 8/2000 | Lipson et al. | |
| 6,200,313 B1 | 3/2001 | Abe et al. | |
| 6,210,355 B1 | 4/2001 | Edwards et al. | |
| 6,733,496 B2 | 5/2004 | Sharkey et al. | |
| 6,949,099 B2 | 9/2005 | Shiro et al. | |
| 7,077,842 B1 | 7/2006 | Cosman | |
| 7,509,175 B2 * | 3/2009 | Sparks et al. | 607/133 |

(Continued)

FOREIGN PATENT DOCUMENTS

| | | |
|---|---|---|
| EP | 1 186 274 A2 | 3/2002 |
| EP | 1 457 162 A1 | 9/2004 |
| JP | 7-265329 | 10/1995 |
| JP | 10-155799 | 6/1998 |

*Primary Examiner* — Michael Peffley
*Assistant Examiner* — Ronald Hupczey, Jr.
(74) *Attorney, Agent, or Firm* — Scully, Scott, Murphy & Presser, P.C.

(57) ABSTRACT

A method of making an incision in an organ includes piercing, by a puncture needle having a proximal end and a distal end, an abdominal wall and an organ that is to be incised, disposing, via the puncture needle, an electrode, to which a first end of a cable is electrically connected, inside the organ, and disposing a second end of the cable outside a body, performing insufflation using a conduit so as to form a space between the abdominal wall and the organ, pulling the cable farther from the second end so that the electrode is placed in contact with an incision position of the organ, and the incision position of the organ is pulled into the space, and supplying power to the cable so that an incision is made by the electrode at the incision position of the organ.

16 Claims, 14 Drawing Sheets

(56) References Cited

U.S. PATENT DOCUMENTS

| | | |
|---|---|---|
| 7,753,928 B2 * | 7/2010 | de la Torre et al. ............ 606/191 |
| 7,988,618 B2 * | 8/2011 | Mikkaichi et al. ............ 600/114 |
| 7,988,656 B2 * | 8/2011 | Uesugi et al. .................. 604/23 |
| 2003/0009085 A1 | 1/2003 | Arai et al. |
| 2004/0172018 A1 | 9/2004 | Okada |
| 2007/0179335 A1 * | 8/2007 | Gertner et al. .................. 600/37 |

* cited by examiner

FIG. 11
FIG. 12
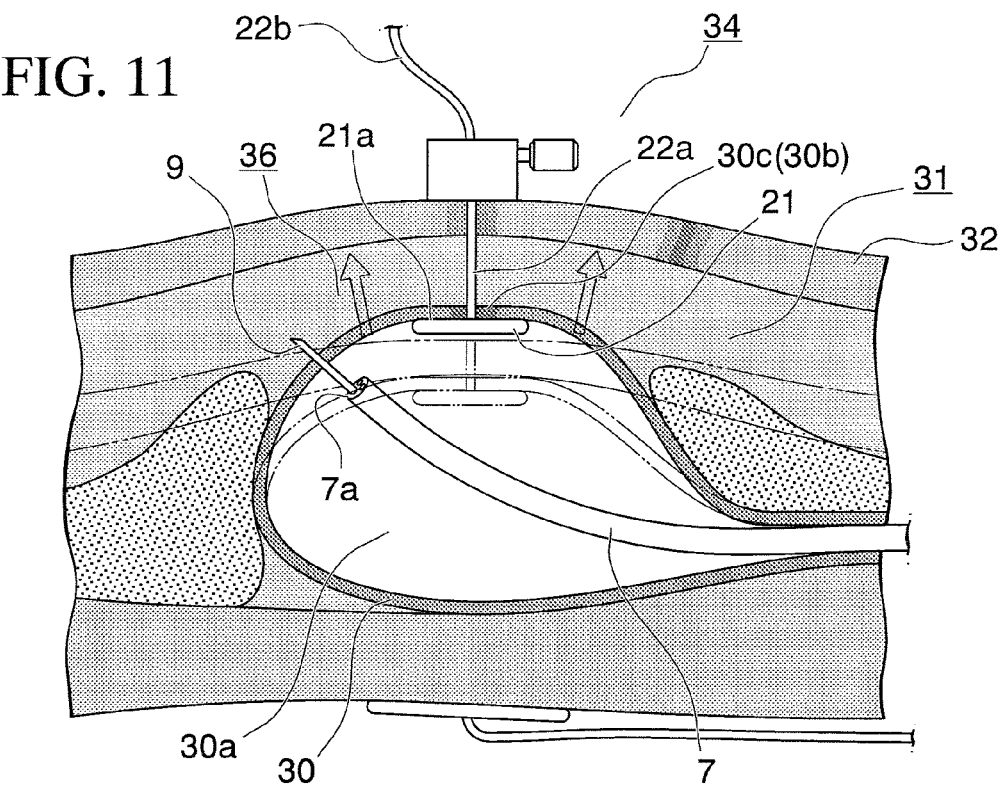
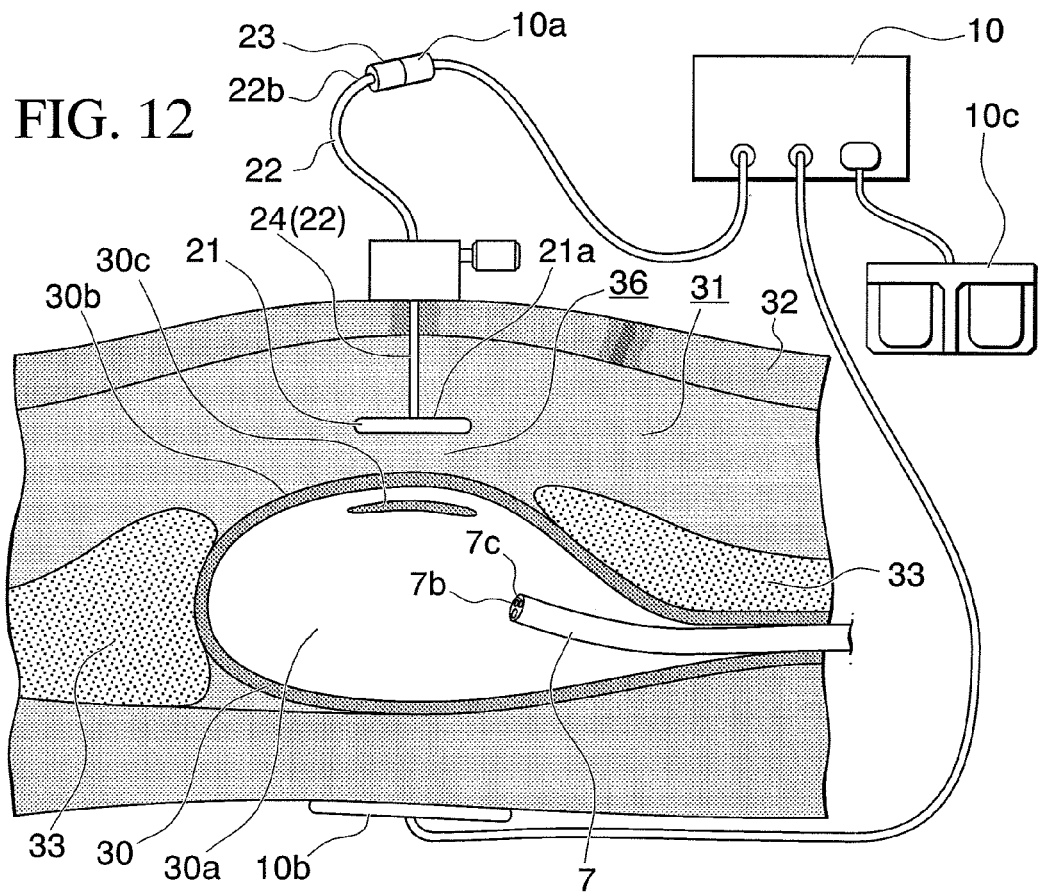

ORGAN INCISION METHOD

CROSS-REFERENCE TO RELATED APPLICATION

This application is a divisional application of U.S. Ser. No. 11/371,455, now abandoned, filed on Mar. 8, 2006, the contents of which are incorporated herein by reference.

BACKGROUND OF THE INVENTION

1. Field of the Invention

The present invention relates to an incision instrument for making an incision in an organ and to an incision apparatus that incorporates the incision instrument, and also to an organ incision method.

2. Description of Related Art

When performing a procedure on an organ in a human body, a laparoscopic operation is known in which, a procedure is performed by opening a plurality of perforations in the abdominal wall and by inserting a rigid laparoscope or a treatment instrument such as forceps in each of the perforations, instead of making a large incision in the abdominal wall. Because only a small perforation needs to be opened, the method has the advantages that there is little invasiveness and the recovery of the patient is rapid.

In addition, in recent years, a method of reducing the degree of invasiveness to a patient even further has been proposed in which a procedure is performed by inserting an endoscope into a natural orifice such as the mouth, nose, or anus of a patient. An example of this type of medical procedure is disclosed in U.S. Pat. No. 5,458,131. A flexible endoscope is inserted via the mouth of a patient who has undergone insufflation. Next, a perforation that is large enough to allow an endoscope to be inserted is formed in the abdominal wall, and the endoscope is sent forward into the body cavity through the perforation.

The endoscope is used for monitoring the interior of the body cavity. An organ is then treated using a treatment instrument that is passed through the endoscope or using a treatment instrument that is passed through another perforation opened in the stomach or a perforation opened in the sigmoid colon through the anus. Once the procedure inside the body cavity has been completed, the treatment instrument is withdrawn and the perforations are closed. In order to close the perforations, the tissue surrounding each of the perforations is suctioned so as to be bunched up and the tissue is then fastened using an O-ring.

SUMMARY OF THE INVENTION

It is an object of the present invention to provide an incision instrument, an incision apparatus that incorporates the incision instrument, and also an organ incision method that make it possible to make an incision more easily in an organ in a body cavity.

The incision instrument of the present invention includes: a substantially rod-shaped electrode that has one end and the other end; a cable that has one end that is electrically connected to the electrode; and a connecting portion that is provided at the other end of the cable and is connectable to a high frequency power supply.

The incision apparatus according to a first aspect of the present invention includes: a puncture needle in which is formed a lumen that extends from a proximal end to a distal end of the puncture needle; an incision instrument that includes a substantially rod-shaped electrode that has one end and the other end, a cable that has one end that is electrically connected to the electrode, and a connecting portion that is provided at the other end of the cable and is connectable to a high frequency power supply, and in which at least the electrode is inserted into the lumen from the distal end of the puncture needle; and a pusher that is inserted into the lumen from the proximal end of the puncture needle and that is adapted to push the electrode of the incision instrument out from the distal end of the puncture needle.

The incision apparatus according to a second aspect of the present invention includes: a flexible sheath; a flexible puncture needle in which is formed a lumen that extends from a proximal end to a distal end of the puncture needle, and that is inserted into the sheath and is adapted to retractably protrude from a distal end of the sheath; an incision instrument that includes a substantially rod-shaped electrode that has one end and the other end, a cable that has one end that is electrically connected to the electrode, and a connecting portion that is provided at another end of the cable and is connectable to a high frequency power supply, and in which at least the other end of the cable is inserted into the lumen from the distal end of the puncture needle; and a pusher that is inserted into the lumen from the proximal end of the puncture needle and whose distal end is engaged by the other end of the cable of the incision instrument, and that is adapted to push the other end of the cable out from the distal end of the puncture needle.

Furthermore, the method of making an incision in an organ of the present invention includes: piercing, by a puncture needle, an abdominal wall and an organ that is to be incised; disposing, via the puncture needle, a substantially rod-shaped electrode inside the organ, and disposing the other end of a cable whose one end is electrically connected to the electrode outside a body through the organ and the abdominal wall; performing insufflation using a conduit that has been introduced into an abdominal cavity so as to form a space between the abdominal wall and the organ; pulling the cable towards the other end side so that the electrode that is connected to the one end of the cable is placed in contact with an incision position of the organ, and the incision position of the organ is pulled into the space that is formed between the abdominal wall and the organ; and supplying power to the cable so that an incision is made by the electrode at the incision position of the organ.

BRIEF DESCRIPTION OF THE DRAWINGS

FIG. 11 is an explanatory view showing a variant example of the insufflation of a body cavity and the drawing back of organs.

FIG. 12 is an explanatory view showing the incision of an organ using an incision instrument.

DETAILED DESCRIPTION OF THE INVENTION

First Embodiment

Figure 1:
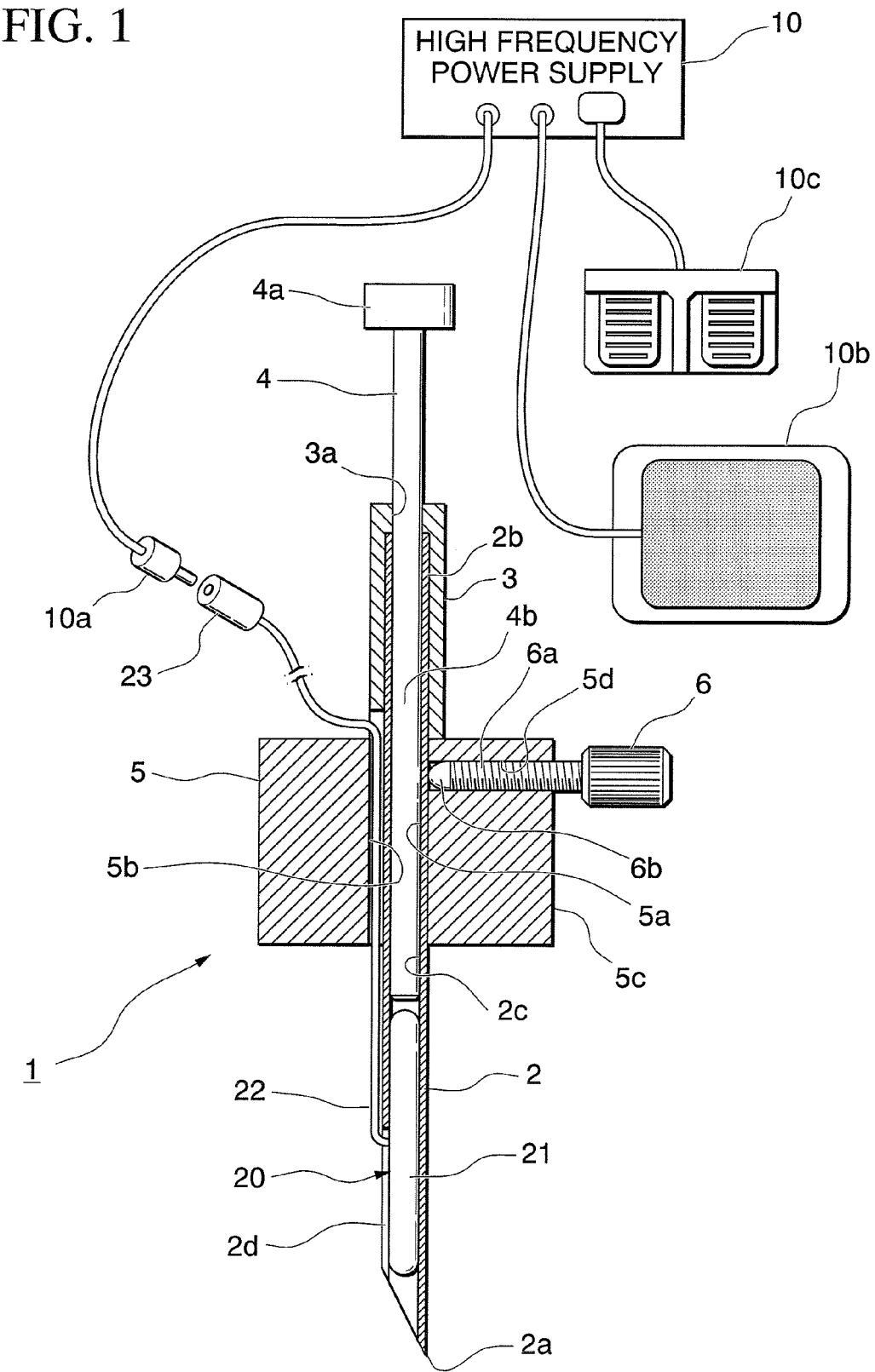
FIG. 1 is an overall view in which a portion has been cut away showing the structure of an incision apparatus according to the first embodiment.

The incision apparatus according to the first embodiment is shown in FIG. 1. As shown in FIG. 1, the incision apparatus 1 has a puncture needle 2 whose distal end 2a has been sharpened to a point and in which a lumen 2c is formed from a proximal end 2b to the distal end 2a. The proximal end 2b of the puncture needle 2 is fitted inside a substantially cylindrical needle holder 3 and the puncture needle 2 is fixed thereto. A through hole 3a is formed in a proximal end portion of the needle holder 3, and the hole 3a is linked to the lumen 2c of the puncture needle 2. Moreover, a pusher 4 that has a stopper 4a at a proximal end thereof is inserted from the proximal end 2b into the lumen 2c of the puncture needle 2 via the through hole 3a of the needle holder 3. A rod-shaped portion 4b of the pusher 4 that is inserted into the lumen 2c of the puncture needle 2 is set so as to be substantially equal in length to the puncture needle 2 or so as to be longer than the puncture needle 2.

Figure 2:
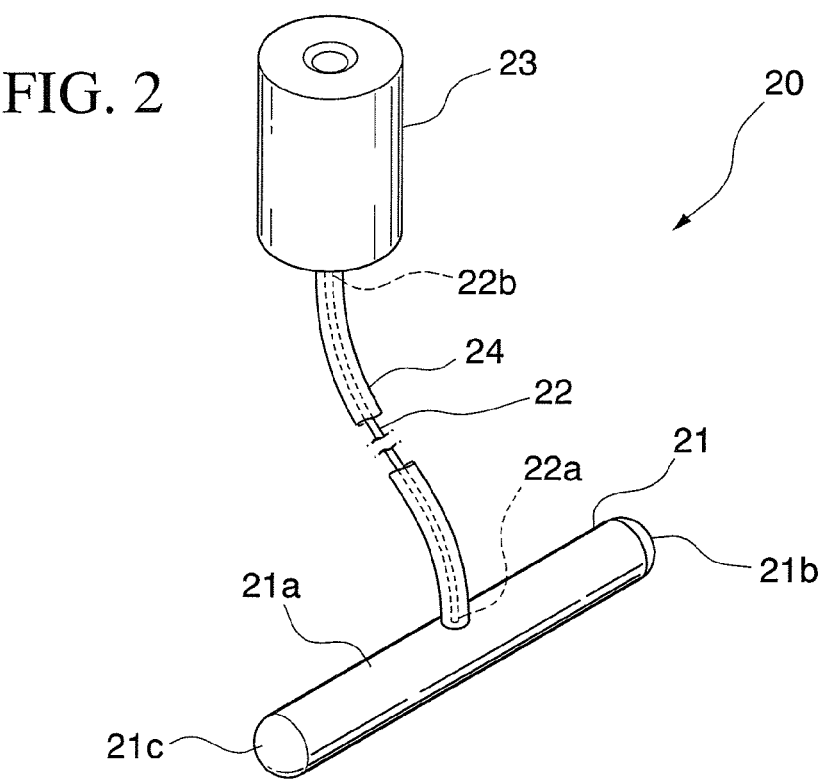
FIG. 2 is a perspective view of an incision instrument of the incision apparatus according to the first embodiment.

The incision apparatus 1 also has an incision instrument 20. The incision instrument 20 has a substantially rod-shaped electrode 21 that has one end 21b and another end 21c, and a cable 22 that is able to conduct electricity. As shown in FIG. 2, a side surface portion 21a is formed between the one end 21b and the other end 21c of the electrode 21. Moreover, one end 22a of the cable 22 is electrically connected to what is substantially the center in the longitudinal direction of the side surface portion 21a of the electrode 21. A connector 23 that is an electrically connectable connecting portion is provided at another end 22b. Except for the one end 22a and the other end 22b, the cable 22 is covered by an insulating tube 24 that provides electrical insulation. As shown in FIG. 1, the incision instrument 20 has a counter electrode 10b that is placed on the surface of a patient's body. A connector 10a of a high frequency power supply 10 is connected to the connector 23, and the counter electrode 10b is provided on the surface of the patient's body. Power is supplied to the incision instrument 20 by the operation of a foot switch 10c and when power is supplied via the electrode 21 to a subject (i.e., to a biological organism), and the subject that is in contact with the electrode 21 can be cut by burning. The current that is supplied via the electrode 21 to the subject is recovered via the counter electrode 10b that is located externally from the body.

Figure 3:
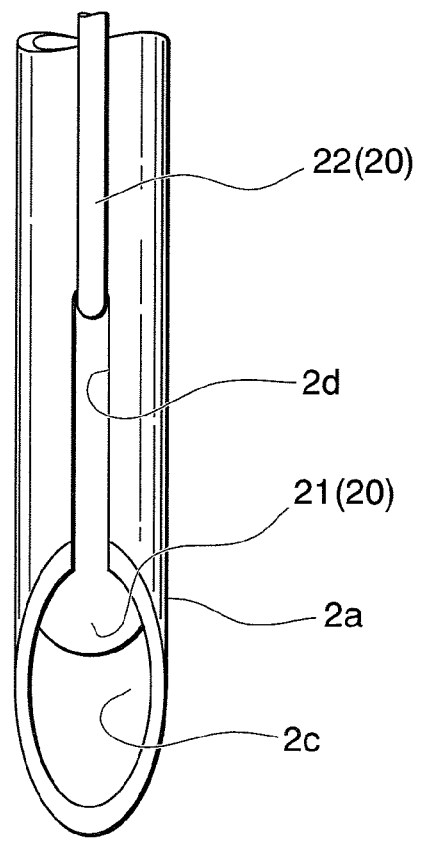
FIG. 3 is an enlarged view of a distal end of a puncture needle of the incision apparatus.

As shown in FIGS. 1 and 3, the electrode 21 of the cutting instrument 20 is also inserted from the distal end 2a of the puncture needle 2 into the lumen 2c, and the cable 22 that is connected to the electrode 21 is positioned such that it extends to the outside of a notch 2d that is formed in the distal end 2a of the puncture needle 2 extending towards the proximal end 2b.

Figure 4:
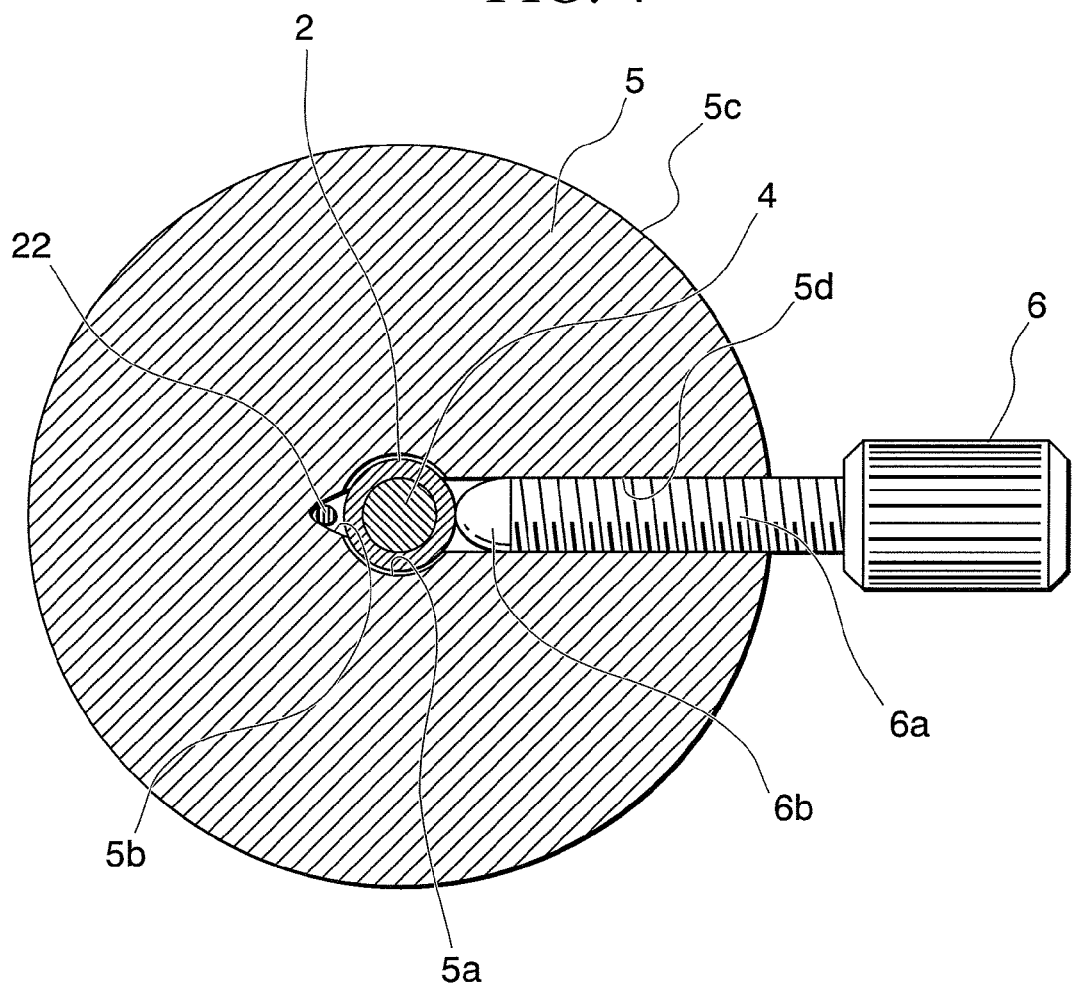
FIG. 4 is a cross-sectional view of an engaging block of the incision apparatus.

Moreover, as shown in FIG. 1, the cutting apparatus 1 has an engaging block 5 that serves as a fixing instrument in which are formed a through hole 5a and a through hole 5b through the center of which it is possible to insert the puncture needle 2 and the cable 22. The through holes 5a and 5b are joined to each other in the radial directions thereof. As shown in FIGS. 1 and 4, a threaded hole 5d is formed extending from a side surface 5c of the engaging block 5 to the side of the through hole 5a that is opposite the through hole 5b, and a locking screw 6 on which is formed a corresponding male thread 6a is threaded into the threaded hole 5d. A convex portion 6b having a blunted distal end is formed at a distal end portion of the locking screw 6. By screwing in the locking screw 6, it is made to push against and consequently engage the inserted puncture needle 2. If the puncture needle 2 is not inserted into the through hole 5a and only the cable 22 is inserted into the through hole 5b, then by further screwing in the locking screw 6, it is possible for the cable 22 to be also pushed against and consequently engaged.

Next, a description will be given of a procedure and of a method of making an incision in an organ of the embodiment. In the section below, as an example of a medical procedure to make an incision in an organ inside a body cavity using the incision apparatus 1, a description is given of an operation to form a perforation in a wall portion of a hollow organ by using the incision apparatus 1 to introduce a device such as an endoscope that is inserted into an abdominal cavity through a natural orifice in a body into a hollow organ (i.e., an internal organ) and then by using the device to perform a desired medical procedure inside the abdominal cavity.

Note that, in this embodiment, a description is given of when a perforation is formed in a stomach wall (more specifically, the front wall of the stomach, or the area on the front side (i.e., the abdomen side) of the greater omentum that hangs down from the greater stomach curvature) in order to enable an approach to the abdominal cavity to be made. Examples of suitable medical procedures that can be performed inside the abdominal cavity include observations, biopsies, extirpations of organs and the like. More specifically, observations inside the body cavity, biopsies and cauterizations of organs (such as livers and pancreases) inside the abdominal cavity, sterilization treatments, and extirpations of appendixes and gall bladders. In order for these medical procedures to be performed using a device such as an endoscope or the like that is inserted through a natural orifice, a perforation is formed in a hollow organ using the incision apparatus 1 in order to allow an approach to be made from the abdominal cavity. However, the hollow organ in which the perforation is formed is not limited to a stomach and may also be a digestive tract other than the stomach such as the large intestine, the small intestine, or the esophagus, or the womb or bladder. Moreover, the natural orifice through which the device is inserted into a body is not limited to the mouth and may also be the nose or anus.

Figure 5:
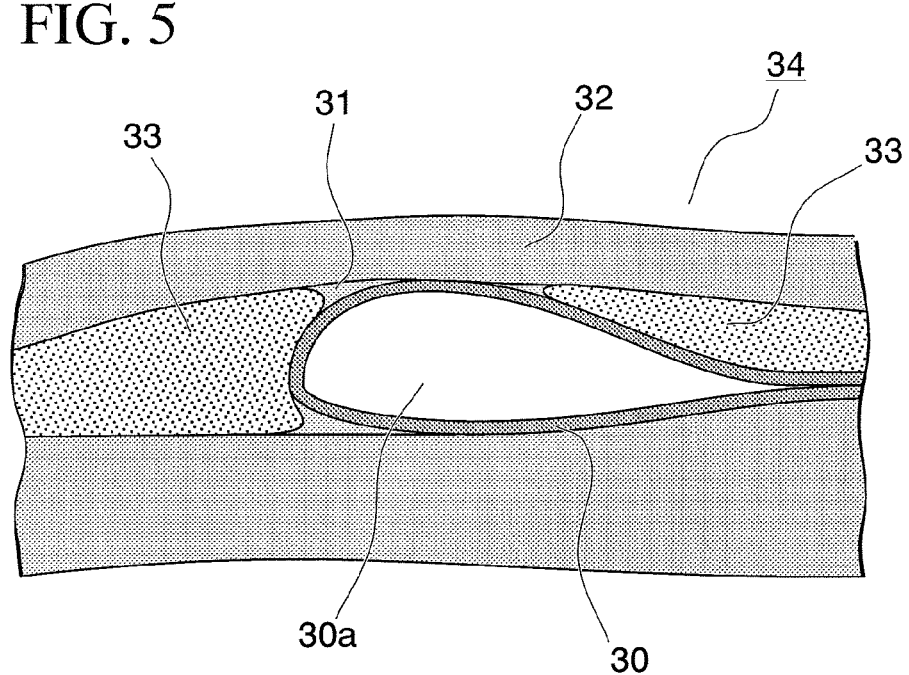
FIG. 5 is an explanatory view showing a state prior to the treatment of an organ.
Figure 6:
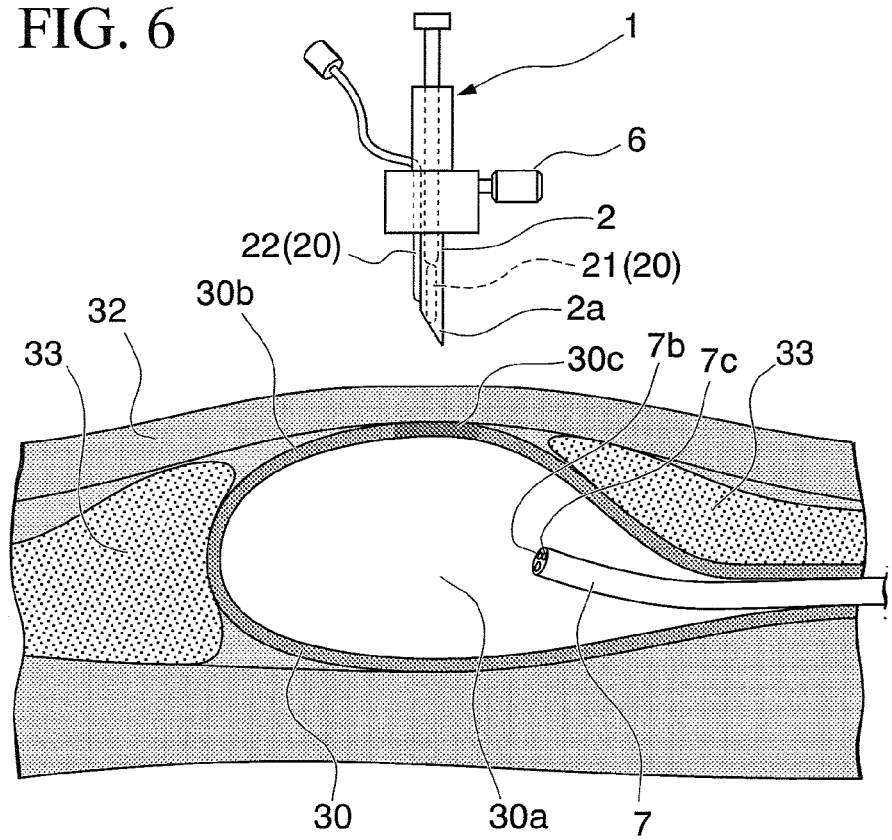
FIG. 6 is an explanatory view showing the piercing of an organ by a puncture needle of the incision apparatus.

FIG. 5 shows a cross section of a human body in the vicinity of the stomach prior to treatment. Prior to treatment, inside an abdominal cavity 31, a stomach 30 is in a state of contact with an abdominal wall 32 and other organs 33 inside the abdominal cavity 31. As shown in FIG. 6, firstly, an insertion portion of an endoscope 7 that has an observation apparatus 7b and a conduit 7c that enables a fluid (such as a gas or liquid) to be supplied to the body interior is introduced through a natural orifice in the form of the patient's mouth into an interior portion 30a of the stomach 30, thereby enabling observations to be made of the interior portion 30a of the stomach 30.

Next, the incision apparatus 1 is prepared. The incision apparatus 1 is in a state in which the electrode 21 of the incision instrument 20 is inserted from the distal end 2a of the puncture needle 2, and the puncture needle 2 and the cable 22 of the incision instrument 20 are inserted in the through holes 5a and 5b of the engaging block 5 and are engaged by the locking screw 6. The stomach 30 is then distended via the conduit 7c (i.e., a conduit that is introduced into an organ from a natural orifice) that is provided in the endoscope 7. Next, the area surrounding the stomach 30 is pressed using fingers from the body exterior 34 and the marks of the fingers are observed using the observation apparatus 7b (i.e., an observation apparatus that is introduced into an organ from a natural orifice) that is provided in the endoscope 7. Based on the observation of the finger marks, the puncture needle 2 of the incision apparatus 1 is then made to pierce the abdominal wall 32 at a position that allows it to penetrate from the abdominal wall as far as an incision position 30c of a front wall 30b of the stomach 30 while avoiding the other organs 33.

Figure 7:
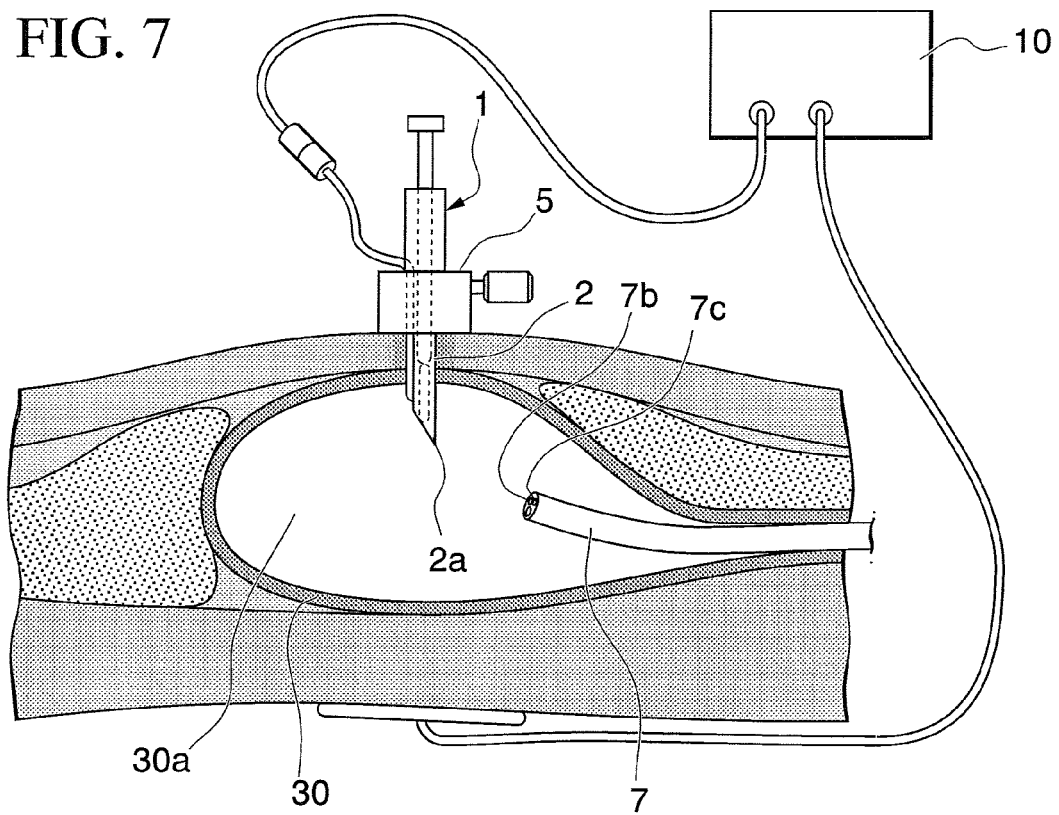
FIG. 7 is an explanatory view showing the piercing of an organ by a puncture needle of the incision apparatus.

As shown in FIG. 7, the puncture needle 2 is then inserted as far as a position where the engaging block 5 comes into contact with the abdominal wall 32, and the distal end 2a of the puncture needle 2 is made to protrude into the interior portion 30a of the stomach 30. Note that the process of causing the puncture needle 2 to pierce the front wall 30b of the stomach 30 is performed while continuously observing the interior portion 30a of the stomach 30 using the endoscope 7.

Figure 8:
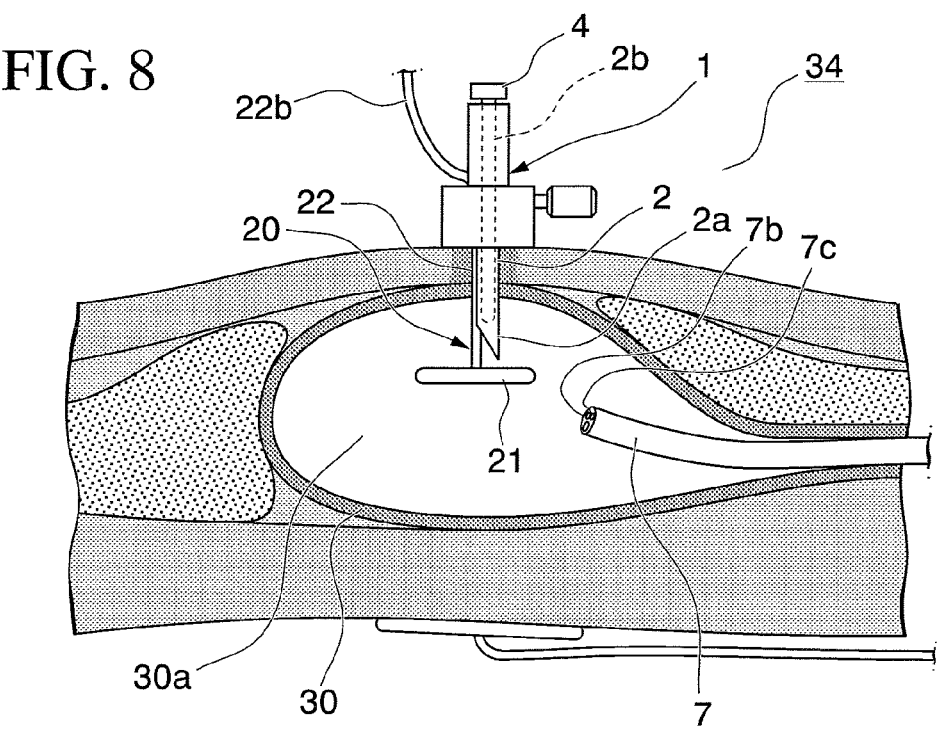
FIG. 8 is an explanatory view showing the positioning of an incision instrument inside an organ.

Next, as shown in FIG. 8, with the puncture needle 2 penetrating as far as the interior portion 30a of the stomach 30 from the body exterior 34, the pusher 4 is further inserted from the proximal end 2b of the puncture needle 2 to the distal end 2a thereof. Consequently, the electrode 21 of the incision instrument 20 is pushed out from the distal end 2a of the puncture needle 2. As a result, the electrode 21 of the incision instrument 20 is positioned in the interior portion 30a of the stomach 30, and the cable 22 passes through the portion pierced by the puncture needle 2, namely, is inserted through the stomach 30 and the abdominal wall 32, while the other end 22b is placed outside the body.

Figure 9:
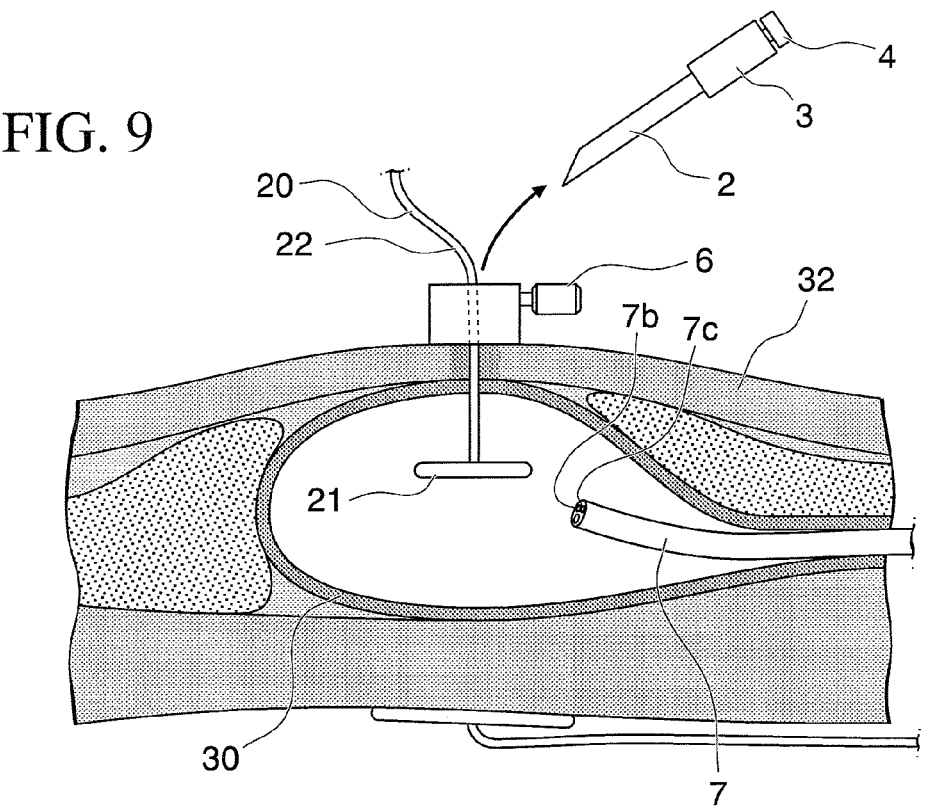
FIG. 9 is an explanatory view showing the positioning of an incision instrument inside an organ.
Figure 10:
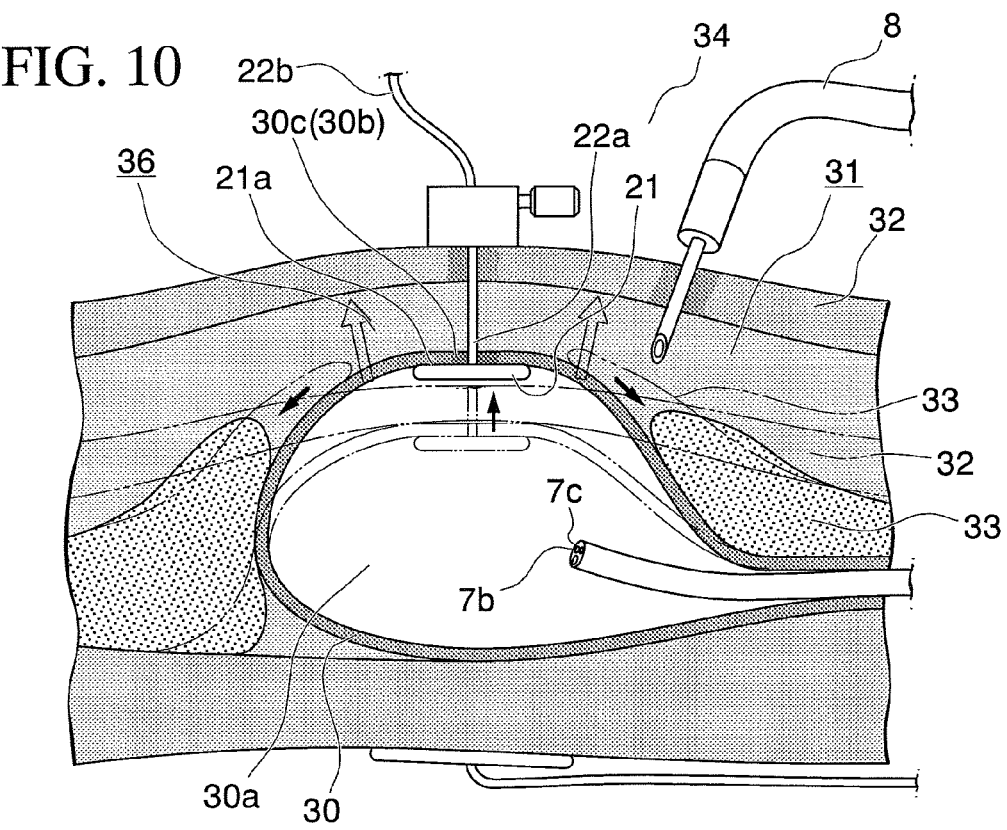
FIG. 10 is an explanatory view showing the insufflation of a body cavity and the drawing back of organs.

Next, as shown in FIG. 9, the locking screw 6 is loosened and the puncture needle 2 is pulled out from the stomach 30 and the abdominal wall 32. After the puncture needle 2 has been pulled out, the locking screw 6 is once again tightened and the cable 22 of the incision instrument 20 is engaged so that it does not drop down. Next, as shown in FIG. 10, an insufflation needle 8 is inserted through the abdominal wall 32 from outside the body and the abdominal cavity 31 is inflated with air. Consequently, a space 36 is formed between the abdominal wall 32 and the stomach 30. Note that the method used for the insufflation is not limited to one in which, as is described above, the abdominal cavity is inflated from the body exterior 34 via the abdominal wall 32 and it may also be inflated from the interior portion 30a of the stomach 30. Namely, as shown in FIG. 11, an insufflation needle 9 may be inserted from a natural orifice in the form of the patient's mouth via a channel 7a in an endoscope 7 that has been inserted into the interior portion 30a of the stomach 30. The insufflation needle 9 is then made to protrude from the distal end of the insertion portion of the endoscope 7 and pierce the stomach wall 30b of the stomach 30, thereby enabling the abdominal cavity 31 to be inflated with air.

In this manner, once an insufflation has been performed using one of the methods described above, the abdominal wall 32 is lifted in the upward direction in the drawings as shown by the arrows in FIG. 10. The cable 22 is fixed to the engaging block 5 that is placed on the surface of the abdomen so that the electrode 21 that has been retained inside the stomach 30 acts as an anchor. Because the distance between the position where the cable 22 is fixed to the engaging block 5 and the electrode 21 remains constant, when the abdominal wall 32 is lifted up a portion of the stomach 30 is raised up (or is pulled up) by the electrode 21. Note that, after the insufflation, the stomach 30 may also be raised up by once again loosening the locking screw 6 and pulling the cable 22 of the incision instrument 20, namely, dragging the cable 22 to the other end 22b side.

At this time, by lifting up (i.e., pulling) the front wall 30b of the stomach 30, the other organs 33 that had been in contact with the stomach 30 fall away and only the front wall 30b of the stomach 30 around the electrode 21 is able to protrude into the space 36.

Finally, as shown in FIG. 12, the connector 23 at the other end 22b of the cable 22 is connected to the connector 10a of the high frequency power supply 10. The counter electrode 10b of the incision instrument 20 is also connected to the high frequency power supply 10 and this is then placed in contact with an optional part of the patient, for example, the patient's back. In this state, if the foot switch 10c is operated, current is supplied from the high frequency power supply 10 via the cable 22 to the electrode 21 and it is possible make an incision at an incision position 30c (i.e., a position facing the lumen 2c when the electrode 21 is accommodated in the lumen 2c of the puncture needle 2) of the front wall 30b of the stomach 30 that is in contact with the side surface portion 21a of the electrode 21.

At this time, because the cable 22 is insulated by the insulating tube 24, the stomach 30 can be incised without any power being conducted to the abdominal wall 32. Moreover, as is described above, when incising the stomach 30, by inflating the abdominal cavity 31 with air and forming the space 36, the front wall 30b of the stomach 30 and the abdominal wall 32 are isolated from each other. As a result, it is possible to easily incise only the front wall 30b of the stomach 30 and avoid the abdominal wall 32. Moreover, because the front wall 30b of the stomach 30 is drawn into the space 36 and is incised with the other organs 33 dropping down, an incision can be made even more easily while avoiding the other organs 33 in the vicinity of the stomach 30. Furthermore, when making an incision, by selecting the front wall 30b of the stomach 30, then designating the incision position 30c, and then making the incision, the incision can be made while avoiding omental arteries and veins. In addition, as is described above, because it is possible to observe the processing sequence using the endoscope 7 that has the observation apparatus 7b in the interior portion 30a of the stomach 30, making an incision in an organ such as the stomach 30 is made even easier.

Namely, according to the incision apparatus 1 and to the above described incision method, it is possible to easily incise only the front wall 30b of the stomach 30 and avoid the abdominal wall 32 and the other organs 33 by only foaming a small hole in the abdominal wall 32 for inserting the puncture needle 2 and forming a small hole in either the abdominal wall 32 or the stomach 30 in order to perform the insufflation.

Once a perforation has been formed using the incision apparatus 1, the endoscope 7 is introduced into the abdominal cavity 31 through the perforation and a desired medical procedure, such as that described above, can be performed. Once the medical procedure inside the abdominal cavity 31 has ended, the links to the interiors of the stomach 30 and abdominal cavity 31 via the perforation are closed.

Note that in the incision apparatus 1 of the present embodiment, while the electrode 21 of the incision instrument 20 is in a state of insertion in the lumen 2c of the puncture needle 2 the cable 22 is positioned so as to extend to the outside from the notch 2d in the distal end 2a, however, it is also possible for the cable 22 to be left inside the lumen 2c as far as the proximal end 2b of the puncture needle 2. In cases such as this, after the abdominal wall 32 and the front wall 30b of the stomach 30 have been pierced by the puncture needle 2 and the electrode 21 has been pushed out, it is necessary to pull the cable 22 out from the puncture needle 2. Because of this, it is possible to employ a structure in which the connector 23 is not provided on the other end 22b of the cable 22, and the other end 22b that is not insulated by the insulating tube 24 is used as the connecting portion and is connected to the connector 10a of the dc high frequency power supply 10.

Figure 13:
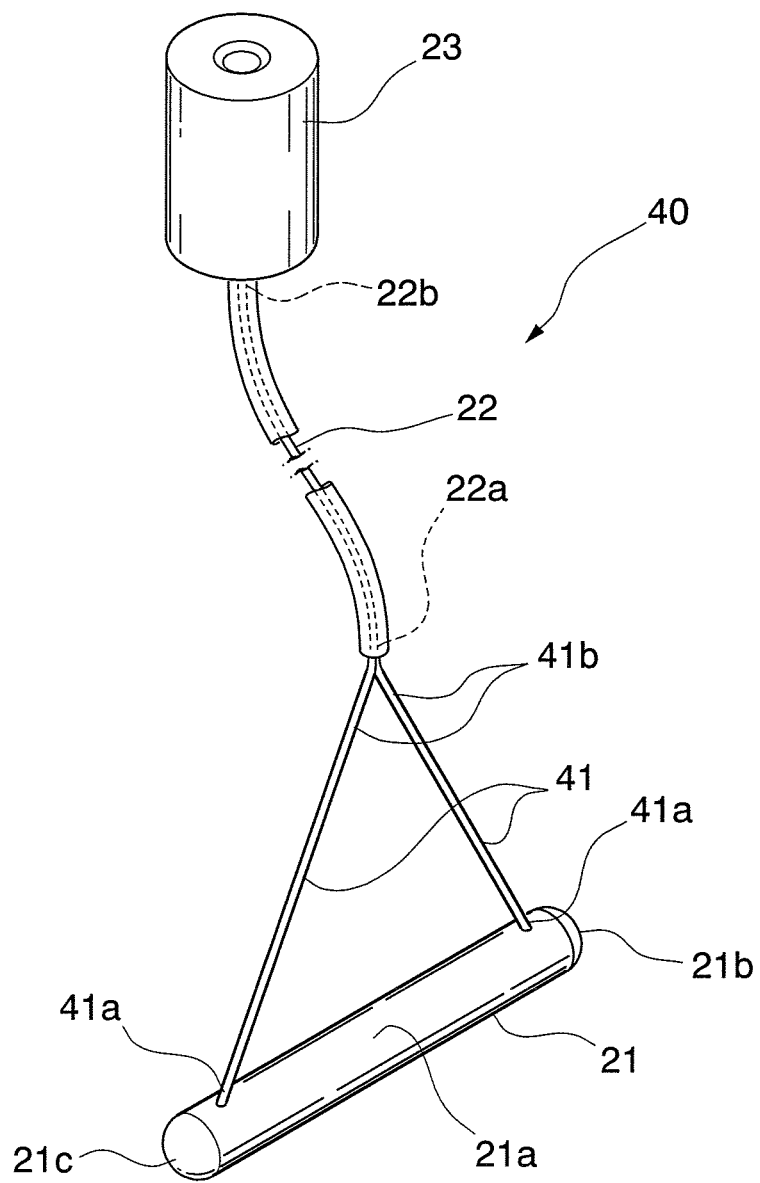
FIG. 13 is a perspective view of an incision instrument according to a variant example of the embodiment.

FIG. 13 shows a variant example of the incision instrument of the present embodiment. As shown in FIG. 13, in the incision instrument 40 of the variant example, the electrode 21 and the cable 22 are electrically connected by two incision cables 41. Specifically, one end 41a of each incision cable 41 is connected is electrically connected to one of the two ends 21b and 21c of the electrode 21 on a side surface portion 21a of the electrode 21. In addition, other ends 41b of each incision cable 41 are both electrically connected to the one end 22a of the cable 22. Moreover, unlike the cable 22, the incision cables 41 are not insulated by the insulating tube 24. Because of this, in this type of incision instrument 40, when power is supplied and the incision of an organ is performed, the incision cable 41 makes contact first with the organ so that the organ is incised gradually. Moreover, because the electrode 21 makes the final contact with the organ, the incision at the incision position can be performed more easily.

Second Embodiment

Figure 14:
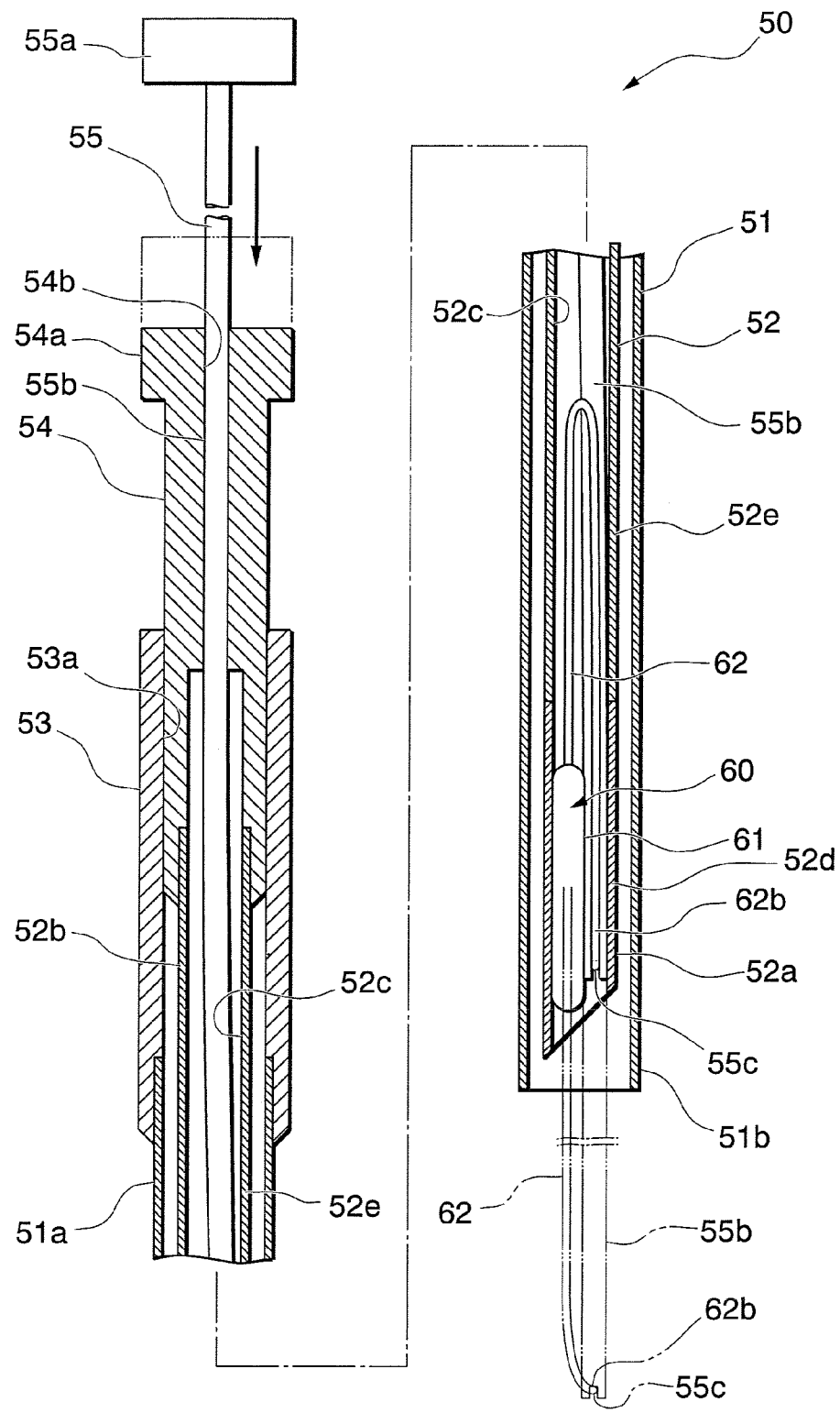
FIG. 14 is a cross-sectional view showing the structure of an incision apparatus according to the second embodiment.

FIG. 14 shows an incision apparatus according to the second embodiment of the present invention. In this embodiment, the same symbols are used for components that are the same as those used in the above described embodiment and a description thereof is omitted.

As shown in FIG. 14, an incision apparatus 50 has a sheath 51 that is flexible and is able to be inserted into the channel of an endoscope, and a puncture needle 52 that is inserted into the sheath 51 and that has a sharpened end 52a. The puncture needle 52 is constructed with a rigid needle member 52d at the distal end of the flexible sheath 52e. A lumen 52c is formed extending from a proximal end 52b to a distal end 52a of the puncture needle 52 and the puncture needle 52 is able to bend together with the sheath 51. A substantially cylindrical gripping member 53 is fitted onto the outside of the proximal end 51a of the sheath 51 and is fixed thereto.

In addition, a substantially cylindrical needle operating portion 54 is fitted onto the outside of the proximal end 52b of the puncture needle 52 and is fixed thereto. A stopper 54a that has an enlarged diameter is formed at a proximal end of the needle operating portion 54. The needle operating portion 54 can be inserted into a through hole 53a in the gripping member 53 until the stopper 54a comes up against the gripping member 53. By moving the needle operating portion 54 backwards and forwards, the puncture needle 52 can be pushed down from the distal end 51b of the sheath 51. A through hole 54b that communicates with the lumen 52c of the puncture needle 52 is also formed in the needle operating portion 54, and a pusher 55 that has a stopper 55a at a proximal end thereof is inserted from the through hole 54b of the needle operating portion 54 as far as the lumen 52c of the puncture needle 52. A rod-shaped portion 55b of the pusher 55 that is inserted in the through hole 54b of the needle operating portion 54 and the lumen 52c of the puncture needle 52 is flexible and is able to bend together with the sheath 51 and the puncture needle 52. The rod-shaped portion 55b is set so as to be longer than the length of the puncture needle 52 and the needle operating portion 54.

Figure 15:
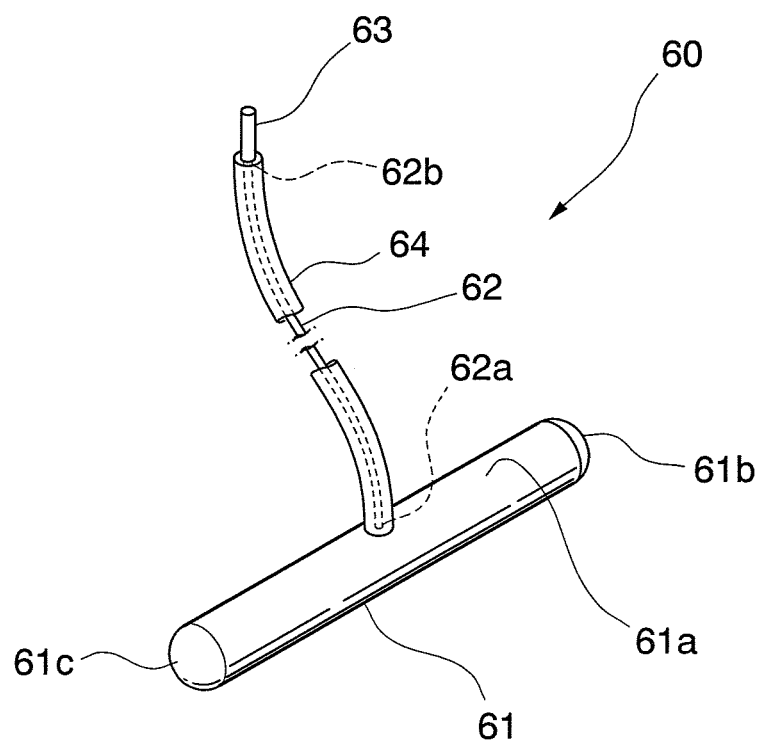
FIG. 15 is a perspective view of an incision instrument of the incision apparatus according to the second embodiment.

The incision apparatus 50 also has an incision instrument 60. As shown in FIG. 15, the incision instrument 60 has a substantially rod-shaped electrode 61 that has one end 61b and another end 61c, and a cable 62 that is able to conduct electricity. A side surface portion 61a is formed between the one end 61b and the other end 61c of the electrode 61. One end 62a of the cable 62 is electrically connected to substantially the center in the longitudinal direction of the side surface portion 61a of the electrode 61. Moreover, the cable 62 is covered by an insulating tube 64 that provides electrical insulation, however, the one end 62a that connects to the electrode 61 and another end 62b that is able to be connected electrically so as to form a connecting portion 63 are in an exposed state.

As shown in FIG. 14, the electrode 61 of the incision instrument 60 is inserted into the lumen 52c so as to be parallel in a radial direction with the rod-shaped portion 55b of the pusher 55 at the distal end 52a of the puncture needle 52. The cable 62 of the incision instrument 60 is also inserted into the lumen 52c of the puncture needle 52, and the other end 62b is engaged with an engaging groove 55c that is formed in a distal end portion of the rod-shaped portion 55b of the pusher 55.

Next, a description will be given of an operation of the incision apparatus 50 and of a method of incising an organ of the present embodiment. In the same way as in the first embodiment, a description is given of when an incision is made in a predetermined position of a front wall of a stomach. Note that, in the same way as in the first embodiment, the hollow organ (i.e., the internal organ) that is being incised is not limited to a stomach, and the natural orifice is also not limited to a mouth.

Figure 16:
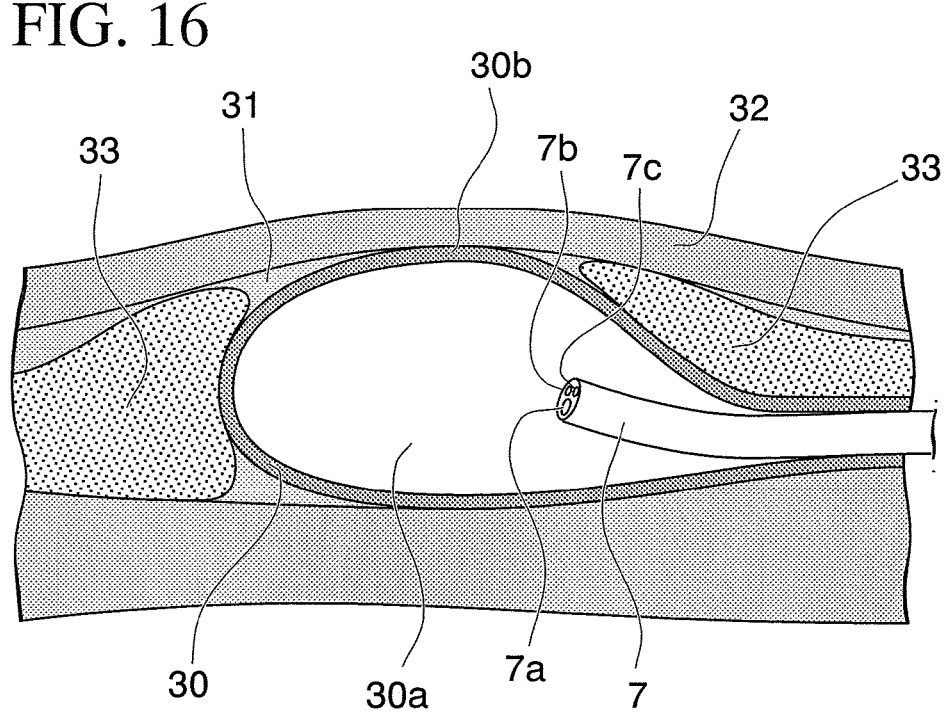
FIG. 16 is an explanatory view showing the piercing of an organ by a puncture needle of the incision apparatus.
Figure 17:
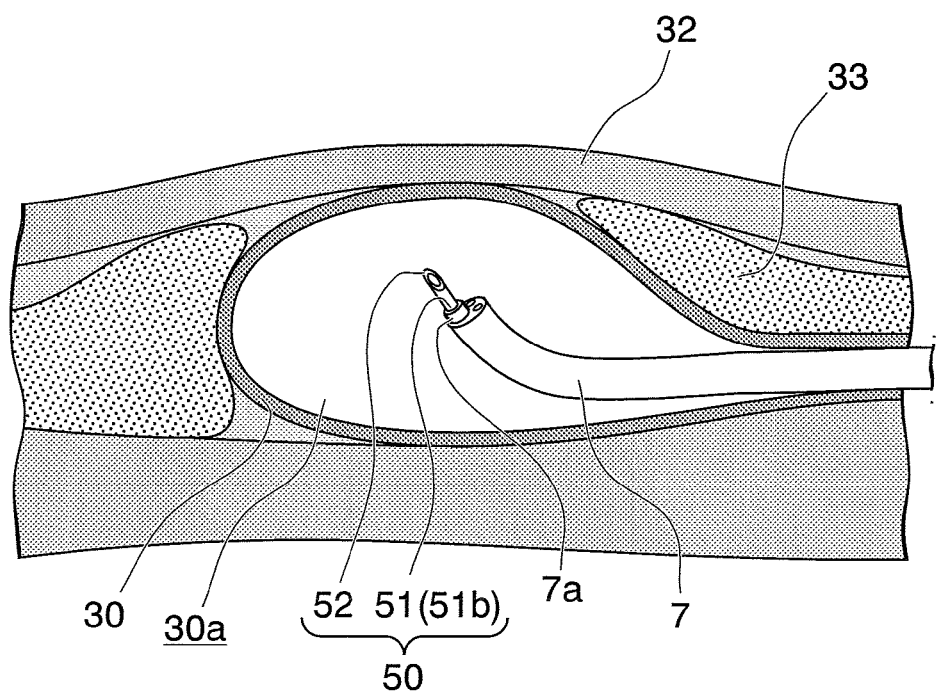
FIG. 17 is an explanatory view showing the piercing of an organ by a puncture needle of the incision apparatus.

As shown in FIG. 16, firstly, the insertion portion of the endoscope 7 that has the observation apparatus 7b and the conduit 7c that is able to supply a fluid (i.e., a gas or a liquid) to the body interior is introduced into the interior portion 30a of the stomach 30 through a natural orifice in the form of the patient's mouth. The stomach 30 is then inflated with air so that observations can be made from the interior portion 30a of the stomach 30. Next, as shown in FIG. 17, the sheath 51 of the incision apparatus 50 is inserted into the channel 7a from the proximal end portion of the endoscope 7 (not shown). The sheath 51 is then made to protrude from the distal end of the insertion portion and, by then further operating the needle operation portion 54, the puncture needle 52 is made to protrude from the distal end 51b of the sheath 51.

Figure 18:
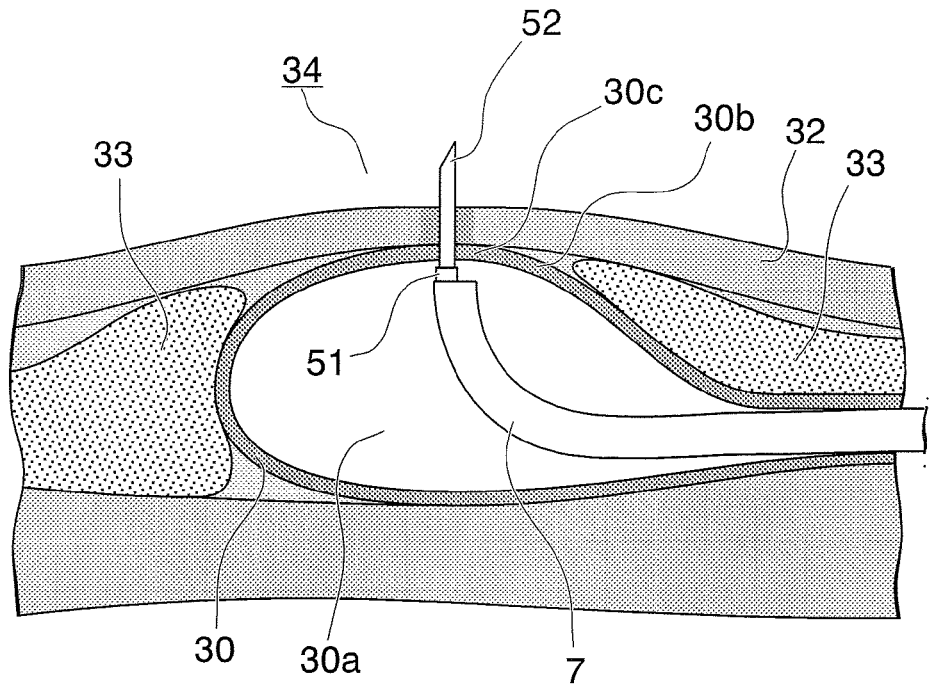
FIG. 18 is an explanatory view showing the piercing of an organ by a puncture needle of the incision apparatus.

Next, the area surrounding the stomach 30 is pressed using fingers from the body exterior 34 and the marks of the fingers are observed using the observation apparatus 7b (i.e., an observation apparatus that is introduced into an organ from a natural orifice) that is provided in the endoscope 7. As a result, it is possible to confirm whether or not the other organs 33 are providing an obstacle. Furthermore, using the observation apparatus 7b of the endoscope 7, the predetermined incision position 30c is confirmed from the interior portion 30a of the stomach 30 and, as shown in FIG. 18, the puncture needle 52 is made to pierce the abdominal wall 32 from the interior portion 30a of the stomach 30 and protrude to the body exterior 34.

Figure 19:
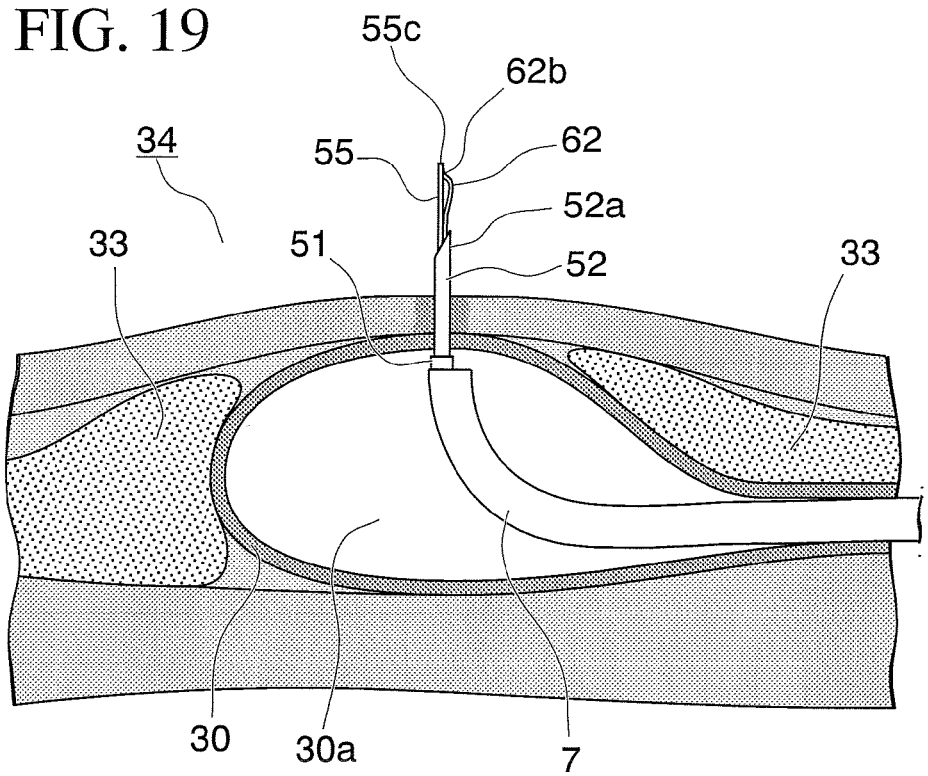
FIG. 19 is an explanatory view showing the positioning of an incision instrument inside an organ.

Next, as shown in FIG. 19, once it has been confirmed from the body exterior 34 that the puncture needle 52 is protruding from the abdominal wall 32, the pusher 55 of the incision apparatus 50 is further inserted from the proximal end 52b of the puncture needle 52 towards the distal end 52a by pushing it at the proximal end portion of the endoscope 7 (not shown). Because of this, the distal end of the rod-shaped portion 55b of the pusher 55 protrudes from the distal end 52a of the puncture needle 52, and, in conjunction with this, the distal end 62b of the cable 62 of the incision instrument 60 that is engaged with the distal end engaging groove 55c is also pushed out. Namely, the other end 62b of the cable 62 is pushed to the body exterior 34 from the interior portion 30a of the stomach 30 and is positioned at the body exterior 34.

Figure 20:
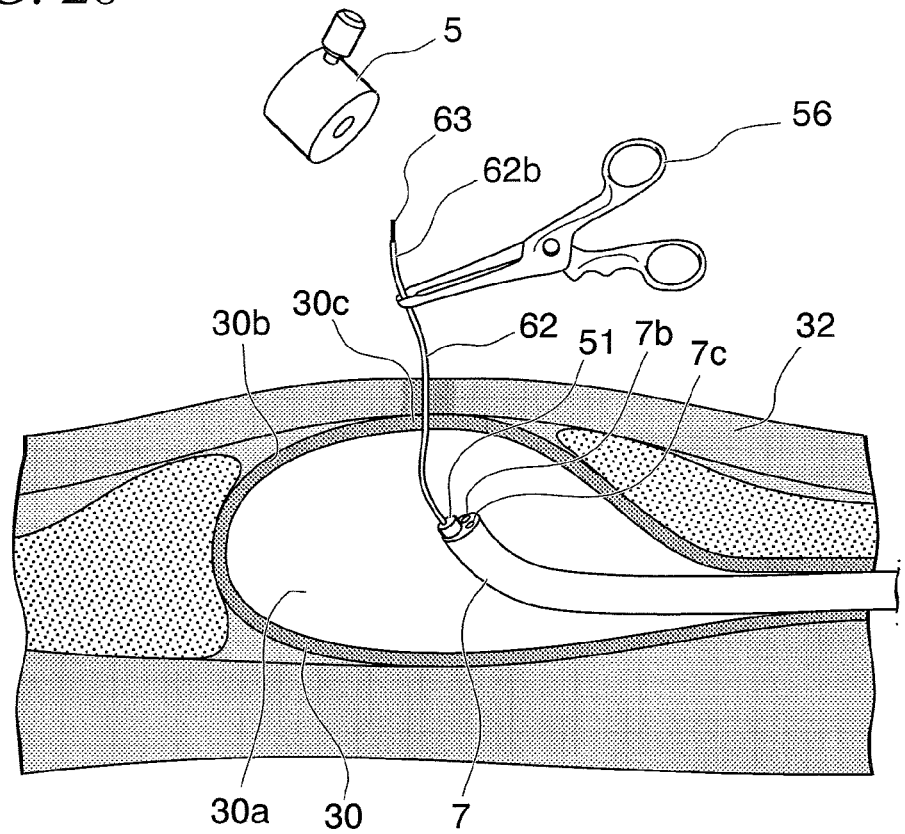
FIG. 20 is an explanatory view showing the positioning of an incision instrument inside an organ.

Next, as shown in FIG. 20, the state of engagement between the pusher 55 and the other end 62b of the cable 62 is terminated, and the cable 62 is gripped by forceps 56. In this state, the needle operating portion 54 of the incision apparatus 50 is again operated at the proximal end portion of the endoscope 7 (not shown) and the puncture needle 52 is pulled out from the abdominal wall 32 and the front wall 30b of the stomach 30 and is pulled back into the interior portion 30a of the stomach 30. Next, by pulling the other end 62b of the cable 62 that is positioned at the body exterior 34 further to the other end 62b side, as shown in FIG. 21, the electrode 61 that is connected to the one end 62a is pulled out from the lumen 52c of the puncture needle 52 and is positioned in the interior portion 30a of the stomach 30.

Figure 21:
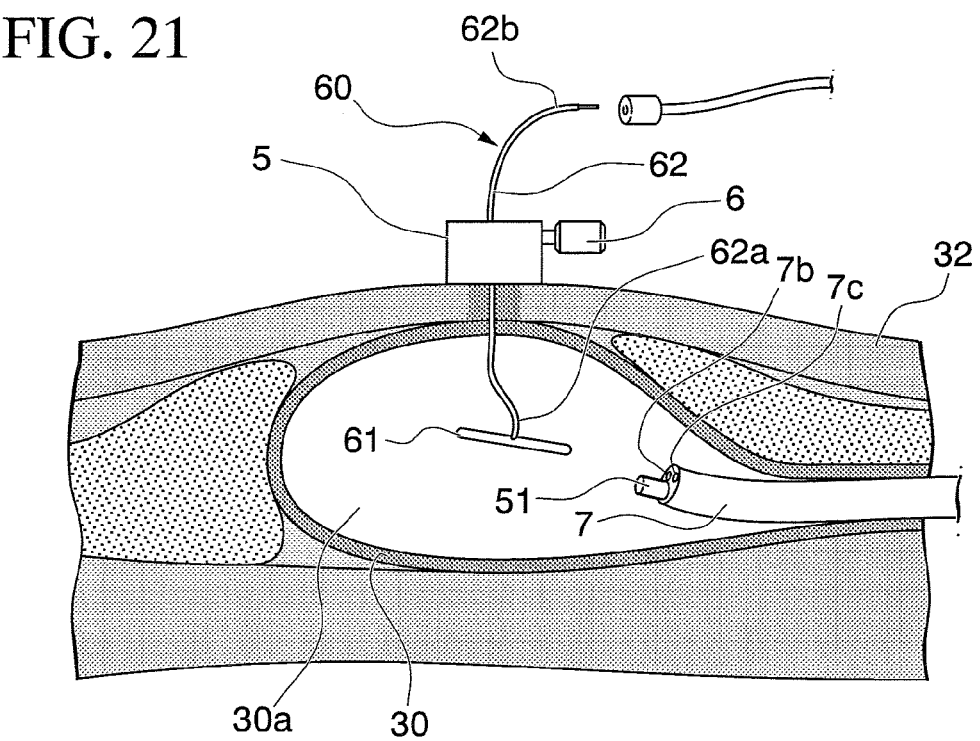
FIG. 21 is an explanatory view showing the positioning of an incision instrument inside an organ.

Next, as shown in FIG. 21, the other end 62b of the cable 62 is inserted into the through hole 5b in the engaging block 5, which serves as a fixing instrument, and the engaging block 5 is made to abut against the abdominal wall 32. In addition, by fastening the locking screw 6, the incision instrument 60 is placed in a reliably fixed state.

Figure 22:
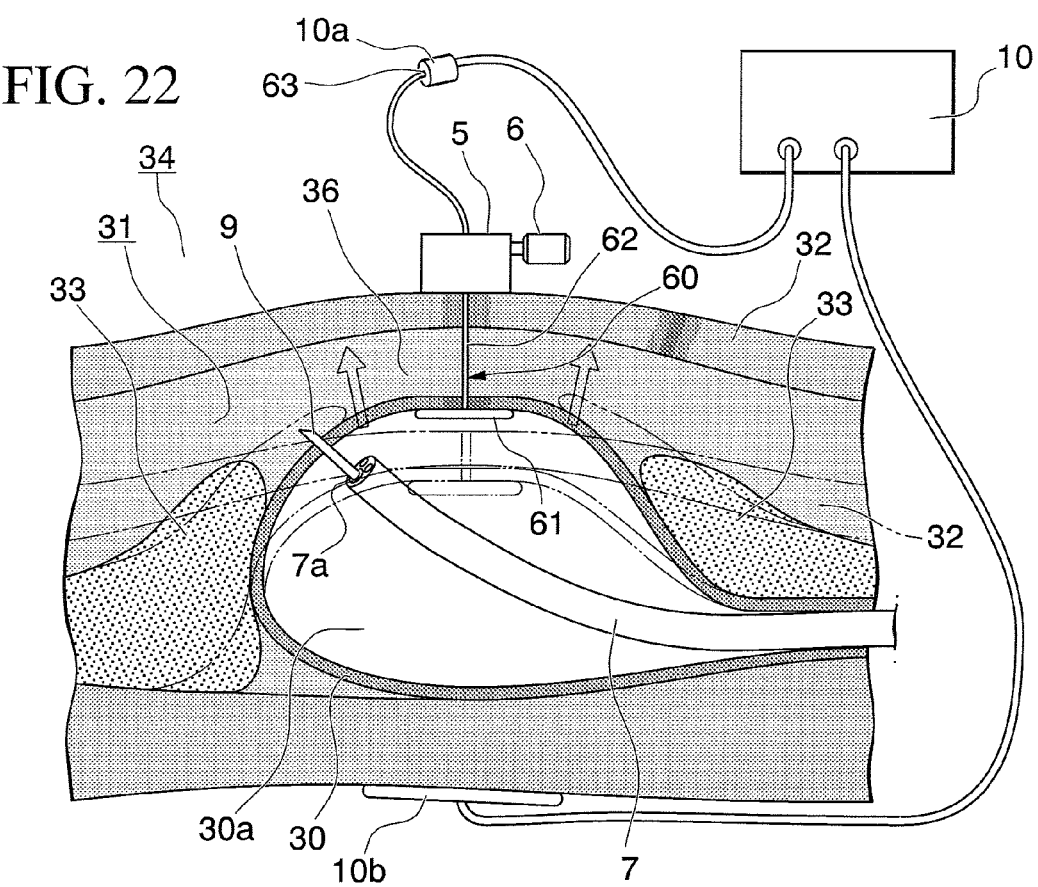
FIG. 22 is an explanatory view showing the insufflation of a body cavity and the drawing back of organs.

Next, as shown in FIG. 22, firstly, the puncture needle 52 and the sheath 51 are withdrawn from the channel 7a of the endoscope 7, and the insufflation needle 9 is inserted. Note that, instead of the insufflation needle 9, it is also possible to use the puncture needle 52 of the incision apparatus 50. Next, based on observations made using the endoscope 7, the insufflation needle 9 is made to pierce the stomach wall 30b of the stomach 30, the abdominal cavity 31 is inflated with air, and the space 36 is formed between the abdominal wall 32 and the stomach 30. Note also that the method used for the insufflation may also be one in which the abdominal cavity is inflated from the body exterior 34 via the abdominal wall 32.

By performing the insufflation in the manner described above, the abdominal wall 32 is lifted in the upward direction in the drawings as shown by the arrows in FIG. 22. The cable 62 is fixed to the engaging block 5 that is placed on the surface of the abdomen so that the electrode 61 that has been retained inside the stomach 30 acts as an anchor. Consequently, because the distance between the position where the abdominal wall 32 is fixed to the engaging block 5 and the electrode 61 remains constant, when the abdominal wall 32 is lifted up a portion of the stomach 30 is raised up (or is pulled up) by the electrode 61. Note that, after the insufflation, the stomach 30 may also be raised up by once again loosening the locking screw 6 and pulling the cable 62 of the incision instrument 60, namely, dragging the cable 62 to the other end 62b side.

Figure 23:
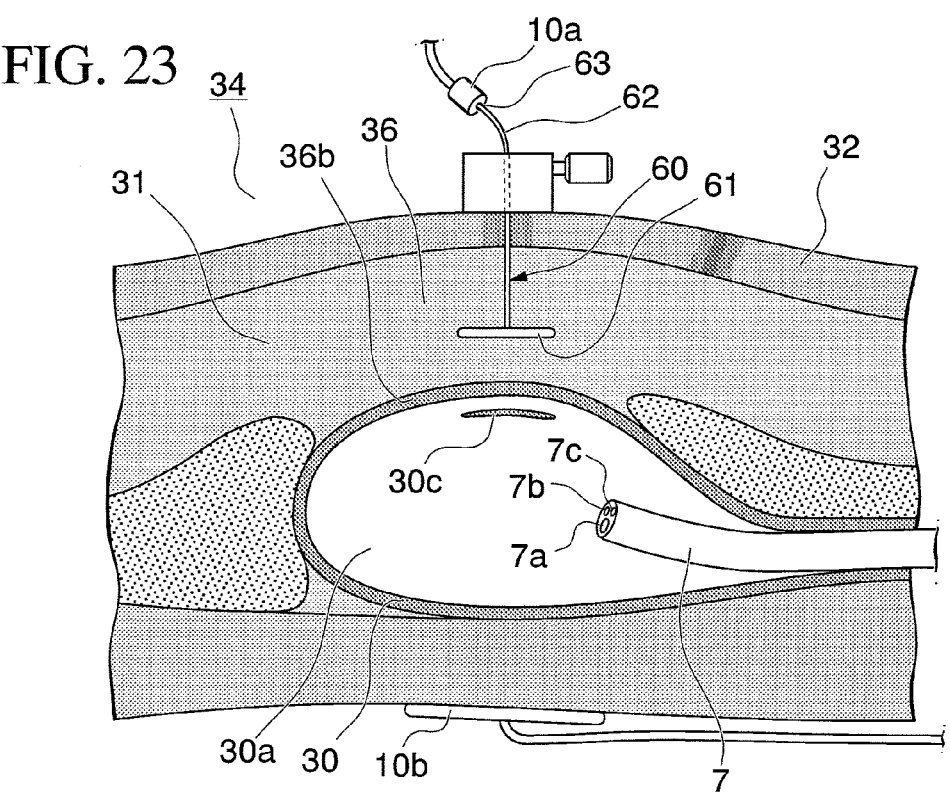
FIG. 23 is an explanatory view showing the incision of an organ using an incision instrument.

Finally, as shown in FIG. 23, the connector 10a of the high frequency power supply 10 is directly connected to the connecting portion 63 of the cable 62 that is protruding to the body exterior 34. If the foot switch is operated while the counter electrode 10b is in contact with the patient's body, current is supplied to the electrode 61 and an incision is made at the incision position 30c of the front wall 30b of the stomach 30.

Once a perforation has been formed, in the same way as in the first embodiment, the endoscope 7 is introduced into the abdominal cavity 31 through the perforation and a desired medical procedure such as that described above is performed. Once the medical procedure has been completed inside the abdominal cavity 31, the links to the interiors of the stomach 30 and abdominal cavity 31 via the perforation are closed.

As has been described above, in the same way as in the first embodiment, it is possible to easily incise only the front wall 30b of the stomach 30 and avoid the abdominal wall 32 and the other organs 33 by only forming a small hole in the abdominal wall 32 for inserting the puncture needle 2 and forming a small hole in either the abdominal wall 32 or the stomach 30 in order to perform the insufflation.

Note that in the present embodiment a structure is employed in which the puncture needle 52 is inserted from the channel 7a of the endoscope 7 that has been introduced through a natural orifice, however, the puncture needle 52 is not limited to this. In addition, in the incision instrument 60, a structure is employed in which the cable 62 is inserted into the lumen 52c of the puncture needle 52 and the other end 62c is engaged in the engaging groove 55c of the pusher 55. At the same time, the electrode 61 is also inserted in the lumen 52c, however, the incision instrument 60 is not limited to this. It is sufficient if at least the other end 62b of the cable 62 is inserted, and it is also possible for a structure to be employed in which the distal end 62a is placed so as to extend to the outside from the distal end 52a of the puncture needle 52, and the electrode 61 is placed in the interior of the sheath 51 outside the puncture needle 52.

Furthermore, in both the first and second embodiments, a description is given of when an incision is made in a front wall 30b of a stomach 30, however, the present invention is not limited to this and may also be applied in the same way to other hollow organs provided that they can be accessed inside the abdominal cavity 31 by forming a perforation, so as to make it possible to make an incision easily.

What is claimed is:

1. A method of making an incision in an organ comprising:
    piercing, by a puncture needle having a proximal end and a distal end, an abdominal wall and an organ that is to be incised;
    disposing, via the puncture needle, a rod-shaped electrode, to which a first end of a cable is electrically connected, inside the organ, and disposing a second end of the cable outside a body through the organ and the abdominal wall;
    performing insufflation using a conduit that has been introduced into an abdominal cavity so as to form a space between the abdominal wall and the organ;
    pulling the cable from the second end so that the electrode that is connected to the first end of the cable is placed in contact with an incision position of the organ, and the incision position of the organ is pulled into the space that is formed between the abdominal wall and the organ; and supplying power to the cable so that an incision is made by the electrode at the incision position of the organ.

2. The method of making an incision in an organ according to claim 1, wherein a lumen is formed in the puncture needle, and the method comprises:
   inserting at least the electrode into the lumen and retaining the second end of the cable at the proximal end of the puncture needle;
   piercing the puncture needle so as to penetrate as far as the interior portion of the organ from the body exterior via the abdominal wall; and
   pushing the electrode out from the distal end of the puncture needle so that the electrode is disposed inside the organ, and the second end of the cable is disposed outside the body through the organ and the abdominal wall.

3. The method of making an incision according to claim 2, comprising: introducing an observation apparatus through a natural orifice into an interior portion of the organ.

4. The method of making an incision in an organ according to claim 1, wherein the inserting of the puncture needle includes making the puncture needle, which has been introduced through the natural orifice of the body into the interior portion of the organ, penetrate as far as the body exterior from the interior portion of the organ via the abdominal wall, and the positioning of the second end of the cable outside the body includes pushing the second end of the cable, which is accommodated inside the lumen that is formed in the puncture needle, out from the distal end of the puncture needle so that the second end of the cable is advanced to the body exterior from the interior portion of the organ.

5. The method of making an incision in an organ according to claim 4, wherein the positioning of the electrode in the interior portion of the organ includes:
   after advancing the second end of the cable to the body exterior from the distal end of the puncture needle in whose lumen the second end of the cable and the electrode have been accommodated, retracting the distal end of the puncture needle into the interior portion of the organ while the electrode is still accommodated inside the lumen; and
   after retracting the puncture needle into the interior portion of the organ, pulling out the accommodated electrode from the lumen.

6. The method of making an incision in an organ according to claim 4, comprising introducing an observation apparatus is through the natural orifice into the interior portion of the organ.

7. The method of making an incision in an organ according to claim 6, comprising:
   introducing an endoscope provided with the observation apparatus through the natural orifice;
   introducing the puncture needle from a channel in the endoscope into the interior portion of the organ; and
   making the puncture needle penetrate as far as the body exterior via the abdominal wall.

8. The method of making an incision in an organ according to claim 1, comprising placing a side surface portion of the electrode in contact with the incision position of the organ.

9. The method of making an incision in an organ according to claim 1, wherein the organ is a stomach.

10. The method of making an incision in an organ according to claim 9, wherein the incision position is at a front wall of the stomach.

11. The method of making an incision in an organ according to claim 1, wherein the insufflation of the abdominal cavity is performed by causing an insufflation needle to penetrate the abdominal wall from the body exterior.

12. The method of making an incision in an organ according to claim 1, wherein the insufflation of the abdominal cavity is performed by inserting an insufflation needle through a natural orifice into the interior portion of the organ and then causing the insufflation needle to penetrate the organ.

13. The method of making an incision in an organ according to claim 1, further comprising:
   introducing a second conduit into the interior portion of the organ through a natural orifice of a body; and
   supplying a gas using the second conduit into the interior portion of the organ so as to inflate the organ, and wherein the making of the puncture needle to penetrate includes making the puncture needle penetrate the organ that has been inflated by the supplied gas and the abdominal wall.

14. The method of making an incision in an organ according to claim 1, wherein the pulling of the cable from the second end includes:
   fixing the second end of the cable to a fixing instrument that is mounted at a fixed position on a surface of the abdominal wall so that a length between the fixed position on the abdominal wall and the electrode is held constant; and
   moving, by using the insufflation, the position on the abdominal wall that is in the vicinity of the fixing instrument relatively to the organ so that the cable is pulled from the second end.

15. The method of making an incision in an organ according to claim 1, wherein the pulling of the cable from the second end includes applying a dragging operation to the cable.

16. The method of making an incision in an organ according to claim 1, further comprising:
   introducing the conduit into the interior portion of the organ through a natural orifice of a body; and
   supplying a gas using the conduit into the interior portion of the organ so as to inflate the organ, and wherein the making of the puncture needle to penetrate including making the puncture needle penetrate the organ that has been inflated by the supplied gas and the abdominal wall.

* * * * *